(12) United States Patent
Kroll

(10) Patent No.: US 6,549,807 B1
(45) Date of Patent: Apr. 15, 2003

(54) IMPLANTABLE CARDIOVERTER DEFIBRILLATOR HAVING A RECHARGEABLE, FAST-CHARGING BATTERY AND METHOD THEREOF

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 116 days.

(21) Appl. No.: 09/709,667

(22) Filed: Nov. 9, 2000

(51) Int. Cl.[7] .................................................. A61N 1/39
(52) U.S. Cl. ........................................................ 607/34
(58) Field of Search .............................. 607/5, 33, 34, 607/61, 29

(56) References Cited

U.S. PATENT DOCUMENTS

| 4,082,097 A | * | 4/1978 | Mann et al. | |
| 5,372,605 A | | 12/1994 | Adams et al. | ................. 607/5 |
| 5,466,254 A | | 11/1995 | Helland | ...................... 607/123 |
| 5,814,075 A | | 9/1998 | Kroll | ............................. 607/5 |
| 5,991,665 A | | 11/1999 | Wang et al. | ................. 607/61 |
| 6,047,211 A | | 4/2000 | Swanson et al. | ............... 607/5 |

* cited by examiner

Primary Examiner—Scott M. Getzow

(57) ABSTRACT

An implantable cardiac device has a pulse generator configured to generate electric shocks for delivery to a patient's heart. The device has an output capacitor, and connected charging circuitry. A first battery is switchably coupled to the charging circuitry, and has a high current flow rate to rapidly charge the capacitor. A second battery is switchably connected in parallel to the first battery, and is operable to recharge the first battery. A detector coupled to the charging circuitry detects when the recharging current is above a predetermined threshold indicative of abnormal recharging. A controller is programmed to enable the charging circuitry to produce the shocks, and to disable the second battery whenever an abnormal recharging current is detected. The controller may operate to connect the batteries on anti parallel whenever an abnormal recharging current is detected.

22 Claims, 9 Drawing Sheets

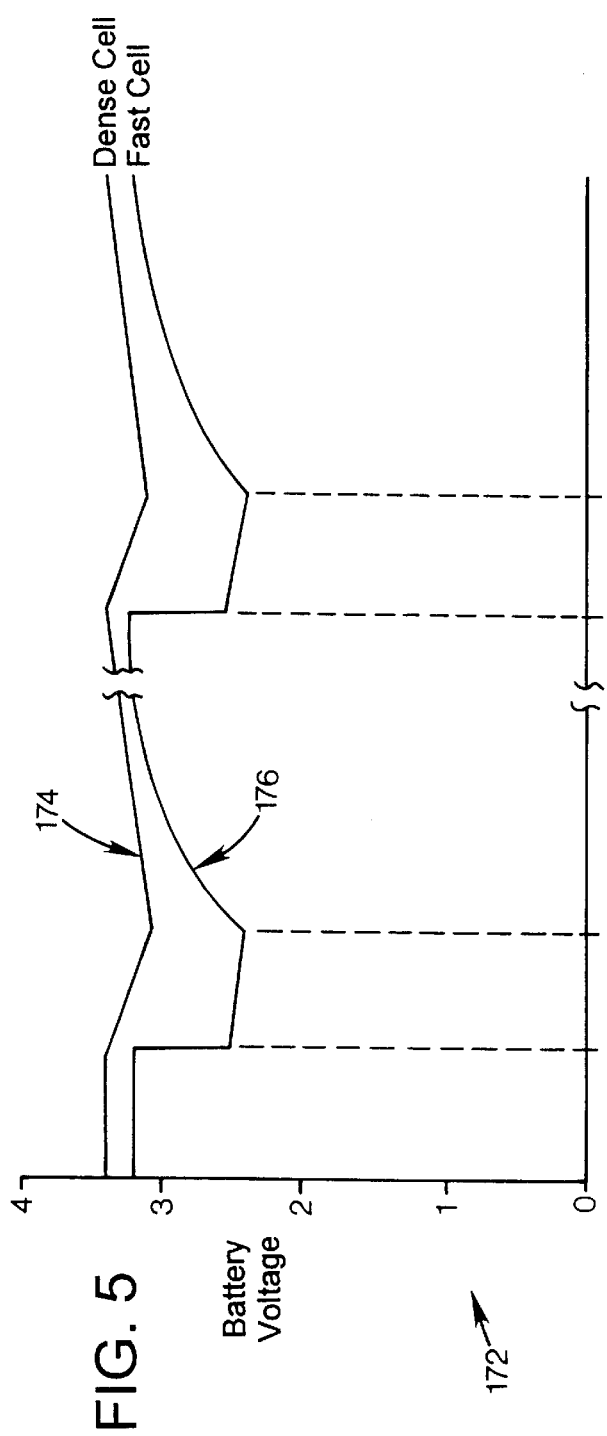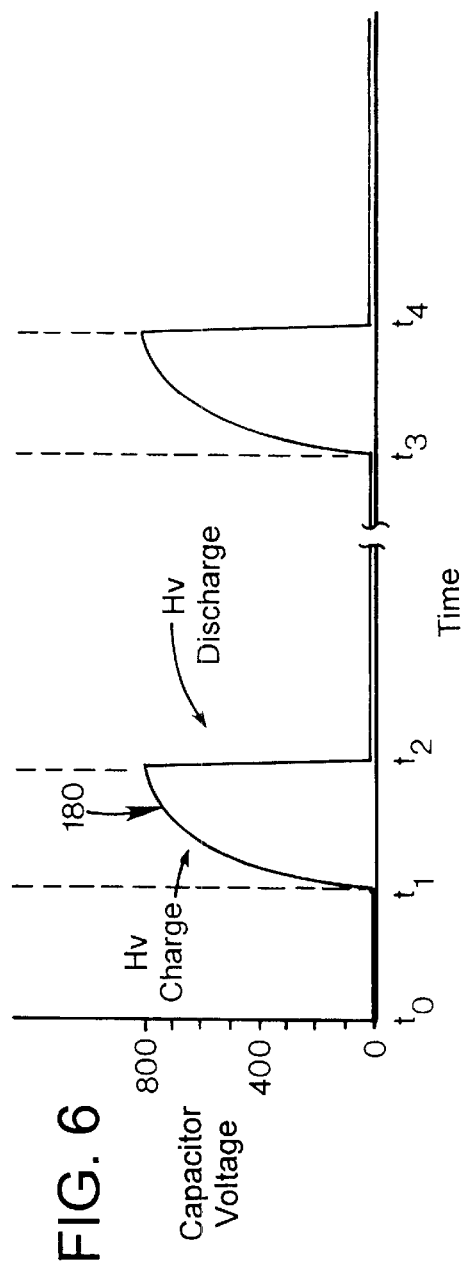

IMPLANTABLE CARDIOVERTER DEFIBRILLATOR HAVING A RECHARGEABLE, FAST-CHARGING BATTERY AND METHOD THEREOF

FIELD OF THE INVENTION

This invention relates to electronic components for implantable medical devices, and more particularly implantable cardioverter/defibrillators having rechargeable fast charging batteries.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by detecting a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

While transcutaneous rechargeable battery systems have been contemplated, for example as provided in U.S. Pat. No. 5,991,665 to Wang et al., such a system has never been implemented in an ICD because of the lack of an acceptable battery recharging system. Therefore, it is generally expected that the battery must store all the energy needed for continuous monitoring and analysis of sensed electrogram and other physiologic signals, for telemetric communications and for potentially numerous shocks over the life of the device, and must retain the energy with minimal leakage to provide a long service life of at least several years, even if not frequently employed for shocks during its life. Thus, the energy storage capacity of the battery is important.

In addition, a battery must be capable of high current rates needed to charge the high voltage capacitors in a short time, so that a therapeutic shock may be delivered within a short time interval after the device has detected and diagnosed a need for the shock. If the battery has an excessive internal resistance, the current flow rate will be limited, delaying capacitor charging. This may result in syncope, ischemia (oxygen starvation) of critical organs and tissues. As a general principle, the sooner the therapy can be delivered following a detected episode, the better prospects are for the patient's health. In addition, it is believed that therapy delivered more promptly requires a lower energy therapy, allowing the conservation of the battery's energy to extend the device life before replacement is required.

Also, an omnipresent concern with implantable devices is device volume. A small device permits more flexibility in implant location, and provides improved patient comfort. There is generally a trade-off between size and storage capacity, with larger batteries providing more capacity. To mitigate this trade-off, batteries with high energy density (watt-hours per unit volume) are desired.

However, there is a trade-off between energy density and the current flow rate discussed above. The highest density cells, such as Mercury-zinc and Silver-zinc types are suited to applications where a moderate current draw occurs, but these have a high internal resistance that prevents them from providing the high current flow rate needed for rapid capacitor charging.

Thus, ICD designers have adopted low internal resistance battery chemistries such as Lithium Silver Vanadium Oxide (SVO), using one or more such cells. These provide the required rapid capacitor charging, but at the cost of somewhat compromised energy density. In addition, SVO and comparable performance batteries are expensive compared to other battery chemistries that lack only the needed current output. Also, over the life of existing devices, as SVO battery voltage diminishes, the time interval between diagnosis of an arrhythmia and completion of capacitor charging increases, so that the effective device life is limited due to the concerns noted above about delayed treatment.

In the past, certain implantable defibrillators were designed to reduce the demand on the battery used for critical, high current charging duties by employing a separate second cell having higher energy density and lower current capacity. This high density cell serves device circuitry not requiring high current rates, reducing the depletion of the lower energy density cell devoted to capacitor charging. While this may permit a slightly extended life, or slightly reduced size, the benefits are limited, because the low current battery circuitry adds size, complexity, and introduces a parasitic current load that will tend to reduce longevity.

In certain rechargeable batteries, including SVO cells used in ICD devices, there remains an inherent concern that uncontrolled recharging can generate elongated dendrites as electrode surfaces are replated, and that in extreme circumstances, these metal dendrites can cause shorting. Shorting in a battery will tend to deplete it rapidly, prevent subsequent recharging, and render the device inoperable. This concern exists regardless of the energy source used for recharging a cell.

SUMMARY OF THE INVENTION

The disclosed embodiment overcomes the limitations of the prior art by providing an implantable cardiac device. The device has a pulse generator configured to generate electric shocks for delivery to a patient's heart. The device has an output capacitor, and connected charging circuitry. A first battery is switchably coupled to the charging circuitry, and has a high current flow rate to rapidly charge the capacitor. A second battery is switchably connected in parallel to the first battery, and is operable to recharge the first battery. A detector coupled to the charging circuitry detects when the recharging current is above a predetermined threshold indicative of abnormal recharging. A controller is programmed to enable the charging circuitry to produce the shocks, and to disable the second battery whenever an abnormal recharging current is detected. The controller may operate to connect the batteries on anti parallel whenever an abnormal recharging current is detected. The invention is also useful for general implantable medical devices, such as nerve or muscle stimulator or even hearing aids or heart pumps.

BRIEF DESCRIPTION OF THE DRAWINGS

Further features and advantages of the present invention may be more readily understood by reference to the following description taken in conjunction with the accompanying drawings, in which:

FIG. 5 is a timing diagram illustrating operation of the preferred embodiment;

FIG. 6 is a timing diagram illustrating operation of the preferred embodiment;

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
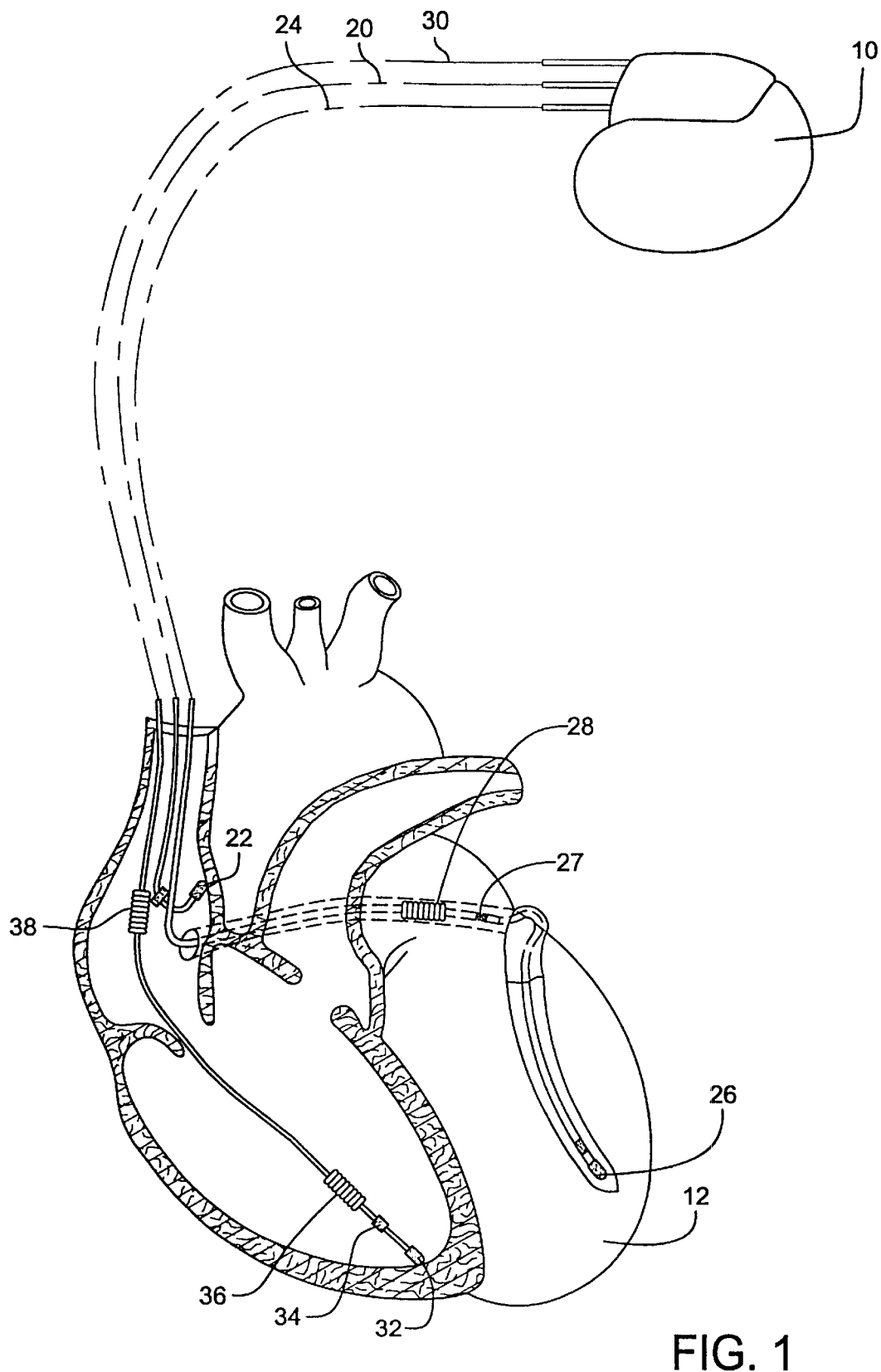
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/547,277, filed Dec. 8, 1999, entitled "Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
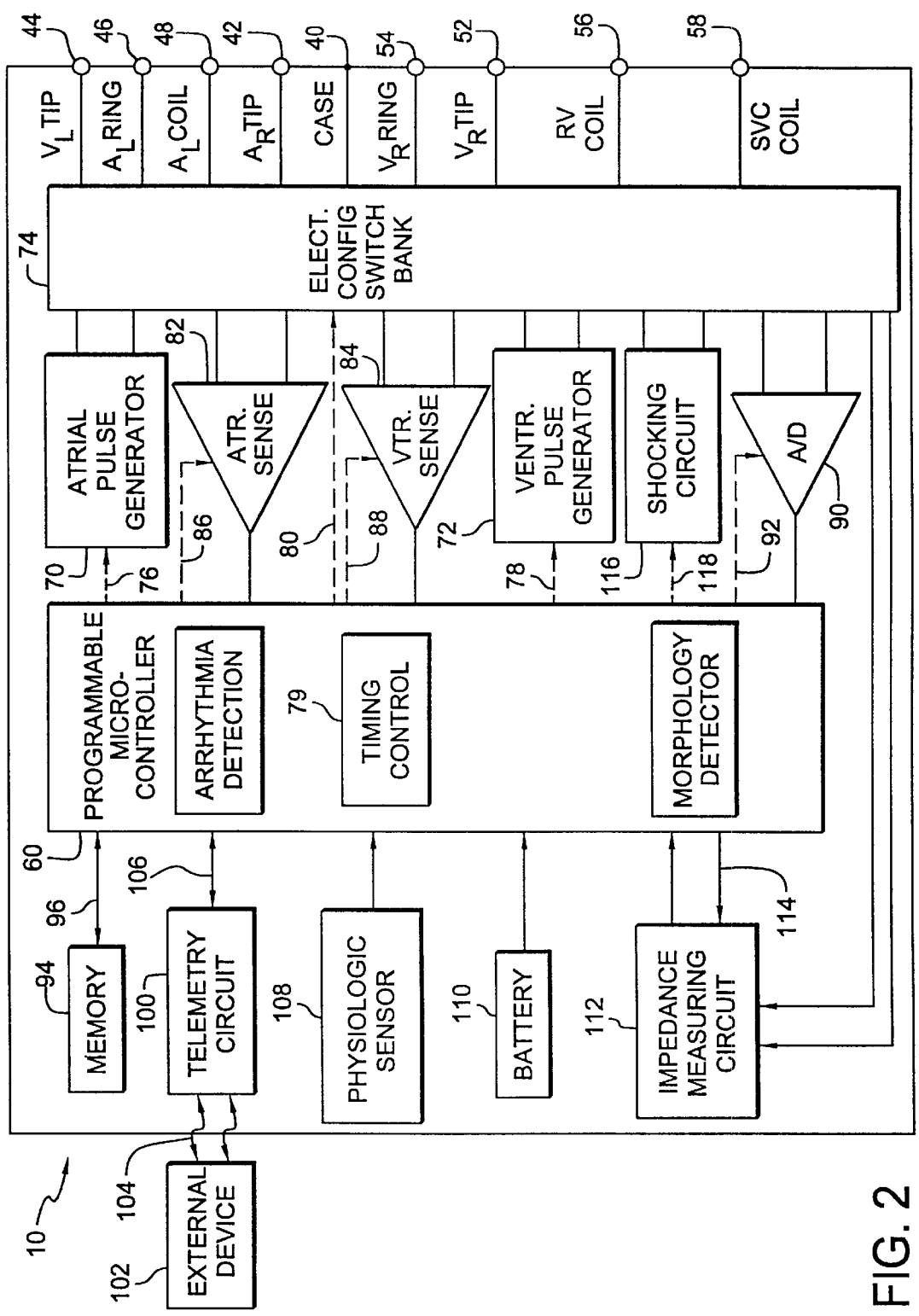
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (A$_R$ TIP) 42 adapted for connection to the atrial tip electrode 22.

To achieve left chamber sensing, pacing and shocking, the connector includes at least a left ventricular tip terminal (V$_L$ TIP) 44, a left atrial ring terminal (A$_L$ RING) 46, and a left atrial shocking terminal (A$_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (V$_R$ TIP) 52, a right ventricular ring terminal (V$_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be noninvasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 µA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
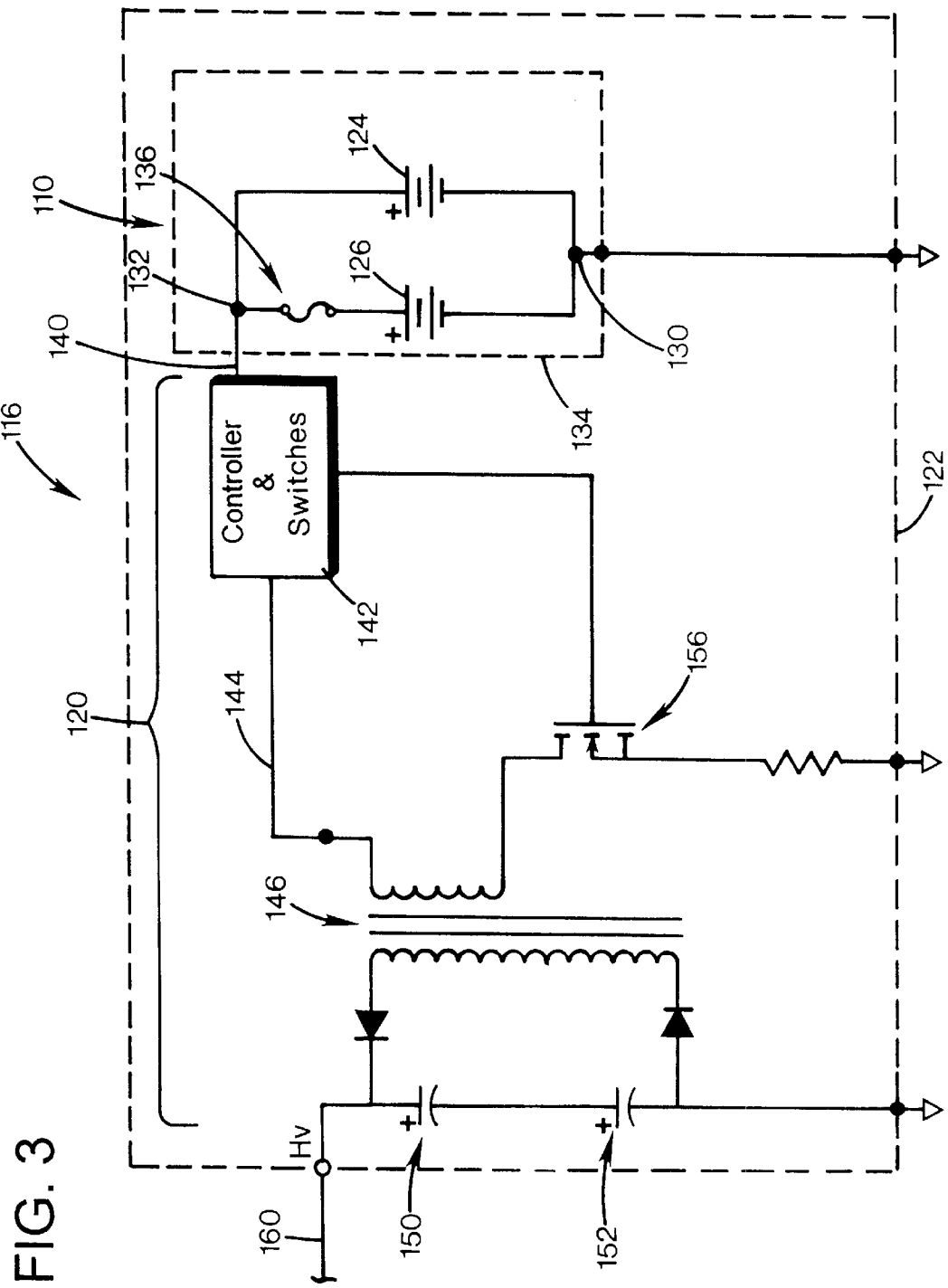
FIG. 3 is a schematic block diagram of output stage circuitry of an implantable defibrillator according to a preferred embodiment of the invention.

FIG. 3 illustrates an implantable cardioverter/defibrillator (ICD) 10 containing a battery network 110 connected to conventional defibrillator circuitry 120, all contained in a metallic conductive housing 122. The battery network 110 includes a first or "dense" cell 124 and a second or "fast" cell 126 connected in parallel between a ground node 130 and an output node 132, with the battery cathodes connected to the ground node 130, and the anodes connected to the output node 132. The ground node 130 is connected to or provided by a conductive metal battery housing 134, which is electrically connected to the device housing 122, which serves as the device ground, and is in electrical contact with a patient in whom it is implanted. An optional current limiting device 136 such as a fuse is connected in line between the fast cell 126 and the output node 124. The battery housing 134 may be provided by a single housing, having two separate chambers for the different cells, or by two separate housings, each containing one of the cells.

An SVO cell that is recharged stores energy by removing lithium anions (Li+) from the cathode to the anode, increasing the voltage of the cell. When energy is drawn from the battery, the material is de-plated, and stored energy is released. A typical SVO cell provides only a narrow spacing between electrodes, which are separated by a polypropylene separator layer. The plating during recharging does not generate a perfectly smooth surface. Small variations in thickness may occur, and in extreme circumstances small spikes or dendrites may extend perpendicularly from the surface of the plated electrode. While small dendrites are tolerable, a dendrite growing through the separator may contact the opposite electrode, causing a short. If charging proceeds after the short first occurs, the connection becomes more robust, and resistance of the dendrite decreases, leading to increasingly rapid discharging of the battery. Such discharging may also discharge a connected source battery of any chemistry as long as charging efforts are continued. Thus, unchecked dendrite growth can damage a rechargeable cell, and deplete all cells, rendering the ICD inoperable.

The cells 124, 126 are connected directly in parallel to each other (the current limiting device 136 merely providing an ohmic connection in normal operating conditions), without any intervening electronic devices such as switches or regulating devices to increase cost, complexity, and/or size. The batteries may be provided as cells in separate compartments of the battery housing 134 or may be provided as separate batteries, each with its own housing.

The battery output node 132 is connected to the circuitry 120 via an output line 140 extending through a sealed passage in the battery housing 134, and is electrically insulated from the housing. The circuitry 120 includes a controller and switching block 142 having a power input connected to the battery output line 140, and includes circuitry needed for pacing, arrhythmia detection, and other needed device functions. The controller has a power output line 144 connected to a DC-to-DC voltage converter 146, which is connected to a pair of high voltage capacitors 150, 152. A control signal line 154 from the controller 142 is connected to the gate of a FET 156 connected between the DC to DC voltage converter 146 and ground, so that a pulsing current may be used to generate a high voltage to charge the capacitors 150, 152. In the preferred embodiment, with battery voltages of about 3V, a potential of up to 800V is developed across the pair of capacitors 150, 152. A lead extends to the patient's heart from a connector in a header of the ICD 10, as illustrated in FIG. 1. The connector is coupled to the high voltage capacitors 150, 152 via lines 160 and 162 and a high voltage output circuit (not shown).

In the preferred embodiment, the dense cell 124 is a Lithium Carbon Monofluoride cell such as are available from Wilson Greatbatch, Ltd. of Clarence, N.Y. with an open circuit voltage of 3.4V at its beginning of life (or discharge), and a theoretical capacity of 1.0–1.5 Amp-hrs. This chemistry has the desired qualities of minimal leakage for a long shelf life, a flat discharge curve that maintains an adequate voltage while its energy is consumed during its useful life, and has a relatively low mass density. The volume of the cell is 3 cc, and the energy density is about 1.3 W-hr/cc. Alternative battery chemistries providing adequate energy density include Mercury-zinc and Silver-zinc and any comparable chemistry existing or yet to be developed with the general characteristics and qualities of relatively high energy density, a relatively low internal resistance, high cathode efficiency, a flat discharge curve, and relatively low mass density. Any chemistry having an energy density of greater than 1.0 W-hr/cc may be considered, as long as it has suitable "dense cell" qualities noted above.

The dense cell 124 has an internal resistance of 20–400 ohms, with 50 ohms being preferred. A resistance below this range would yield an excessive rate at which the dense cell recharges the fast cell 126 after depletion, as will be discussed below, wasting heat energy and potentially causing damage. A resistance above this range would yield an excessive time to recharge the fast cell 126, undesirably delaying the delivery of a subsequent therapy.

The fast cell 126 is preferably a Lithium Silver Vanadium Oxide cell such as are available from Wilson Greatbatch, Ltd. of Clarence, N.Y. with a volume of 3 cc, and an open circuit voltage of 3.2V at its beginning of life (or discharge), which is slightly less than that of the dense cell 124. Because the dense cell 124 has a higher voltage under all operating conditions throughout the device life, it will serve to charge the fast cell 126 when the fast cell 126 is occasionally used for capacitor charging and at least partially depleted, as will be discussed below. The voltage difference between the cells 124, 126 is limited to a small fraction of their voltages so that the charge rate is limited to prevent overheating and damage while recharging the fast cell 126. Also, the small voltage difference is preferably about 0.3–0.4V, which leads to a desirable trickle charge or topping off of the fast cell 126 by the dense cell when the fast cell 126 has been used. As noted above, the limited voltage difference provides an inherent current limitation between the cells, so that undesirable current or voltage regulation components are not needed, and the cells may simply be hardwired in parallel to each other as shown.

In the preferred embodiment, the fast cell 126 has an open circuit voltage 94% of that of the dense cell 124, although this number may range between 70% and 95%. The fast cell 126 has a loaded voltage of 2.5V, which is the approximate voltage when the fast cell 126 is connected to the low resistance load of the DC-to-DC converter 146.

The fast cell 126 has a theoretical capacity range of 0.3–0.7 Amp-hrs, which is less than that of the dense cell 124 by a factor of 1.4 to 5.0. While some advantages of the invention may be achieved with a dense cell 124 having a capacity less than or equal to that of the fast cell 126, the cost, size, and product life advantages are best served by a dense cell 124 with greater capacity than the fast cell 126. The fast cell 126 need only have adequate capacity to provide energy for 10 to 30 capacitor charges; the dense cell 124 is sized with a capacity to serve an expected life, both in terms of shelf life years, and in terms of a total number of therapy shocks delivered. The dense/fast capacity ratio may be increased for applications in which a very long product life is required (and increased size is tolerated), or for devices using lower-energy therapy techniques. The ratio may be smaller for devices needing only a limited life, where smaller device size is needed, and/or where therapy requires greater energy discharge.

The fast cell 126 has an internal resistance of 0.5–3.0 ohms, which is less than that of the dense cell 124 by a factor in the range of 17–1000, leading to a corresponding difference in current flow rate capability under a comparable load. In the preferred embodiment, this resistance ratio is in the range of 20–100, and 40 is considered optimal. In the preferred embodiment, the resistance of the fast cell 126 changes tolerably over the device life, beginning at 0.8 ohms, reducing to 0.5 ohms in the middle of life, and increasing above 1.0 ohms at the end of life.

Alternative fast cell 126 chemistries include Lithium Ion with a Cobalt-based cathode, and any comparable chemistry existing or yet to be developed with the general characteristics and qualities of very low internal resistance yielding a high current carrying capability, an energy density that is about one half that of the dense cell's 124, and a low leakage rate.

In the preferred embodiment, the fast cell 126 has a lithium anode, while the alternative embodiment discussed below has a fast cell 126 with a carbon anode. Historically, Lithium Silver Vanadium Oxide cells have been used in implantable defibrillators due to their high current carrying capability. However, recharging cells with lithium anodes has previously been avoided in many applications, for the following reasons. Cells with lithium anode technology are relatively expensive, are used in very special applications, and are not readily adopted when well known and characterized technologies are desired. In addition, lithium anode technology could be potentially dangerous in some applications, because recharging of such a cell at excessive rates can cause overheating and product damage. Thus, the recharging of lithium anode cells has been avoided for use in implantable medical devices due to the possible risk. However, the preferred embodiment inherently avoids the risk of overcharging by using one battery (of limited voltage and current) to charge the fast cell 126. There is no way for the fast cell 126 to receive a higher voltage than is provided by the dense cell 124, unlike other applications where a charge rate regulator may fail and lead to damage or injury.

Figure 4:
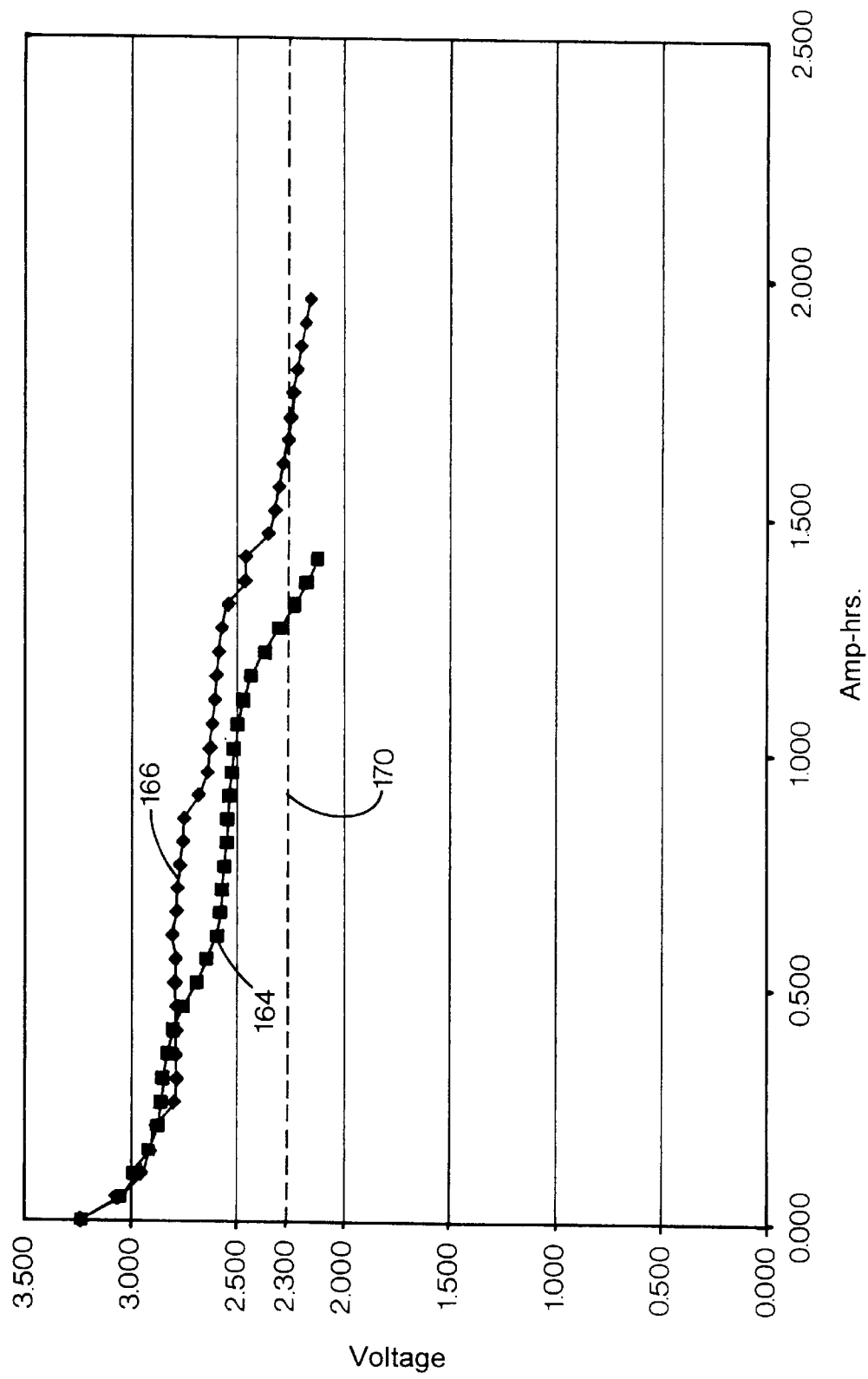
FIG. 4 is a graph illustrating operating performance of the preferred embodiment in comparison to a prior art device.

FIG. 4 illustrates the performance difference between the preferred embodiment system using the different battery chemistries, and a prior art conventional battery system using two identical SVO or fast cells 126. The tested battery systems have essentially the same volume e.g. of (3+3=) 6 cc, so that performance differences are attributable to the chemistry differences and not size. For each battery, the experiment was conducted by repeatedly placing a load on the batteries, causing them to charge a capacitor circuit as in an actual device. Such a charge is drawn every two hours during the experiment, and lasts 10 to 30 seconds, with the batteries being dormant for most of the two-hour period. The indicated voltage is the open circuit voltage measured prior to a capacitor charge, and not during the time the load is applied.

Line 164 indicates the prior art dual-SVO battery, and line 166 indicates the hybrid battery of the preferred embodiment; the voltage is indicated on the vertical axis, and power consumed (in Amp-hrs) is indicated on the horizontal axis. The total energy delivered is indicated by the area under each curve. An open circuit voltage threshold of 2.3V is indicated by threshold line 170. This threshold is considered the minimum voltage needed by the battery to charge the capacitors in a suitably brief time of no more than 30 seconds after an arrhythmia is diagnosed. When the battery voltage has dropped below this level, the device is considered to be at the end of its useful life, and is due for replacement.

As indicated, the preferred embodiment indicated by line 166 has an operating life greater than the prior art battery indicated by line 164, and drops below the voltage threshold at about 1.6 amp-hours as compared to 1.25 amp-hours for the dual SVO device. Thus, in a package of the same size, product life is extended by about 30%. In addition, it is notable that the slope of the line 166 as it passes below the threshold is gentler than that of the prior art line 164 as it passes below the threshold, indicating that where lower thresholds are tolerated, the difference in life becomes even greater.

The illustrated experiment is very conservative, and is more demanding than normal usage. It simulates a patient receiving the delivery of therapy every two hours for a period of weeks, which would be an extraordinary medical circumstance. More typical uses involve extended periods of days, weeks, months, or years between therapy events, allowing the cells to fully recover and equilibrate in a manner that is believed to increase the performance life differences between the two tested battery configurations. The capacitor charge duration varies only minimally as needed to ensure a full charge, with charges late in a battery's life taking slightly longer. For clarity, it is important to note that the batteries are not charged; the "charging" referred to herein is the charging of the capacitors, caused by discharging of the batteries.

FIGS. 5 and 6 show a timing diagram 172 of the operation of the preferred embodiment of the invention during two incidents of high voltage capacitor charging and discharging to provide therapy for an arrhythmia. The diagram has an upper part indicating the voltages of the batteries over time, and a lower part indicating the capacitor voltage over the same time scale. Line 174 indicates the voltage across the dense cell 124 20, line 176 indicates the voltage across the fast cell 126, and line 180 indicates the voltage potential of the output line 160. Critical moments in time are indicated by $t_0$, $t_1$, $t_2$, $t_3$, and $t_4$.

During the $t_0$–$t_1$ interval, the batteries are at their open circuit voltages indicated above, with the dense cell's 124 slightly greater voltage providing a continual topping off of the fast cell 126 to ensure that the fast cell 126 is maximally saturated. The capacitor is at zero voltage, avoiding the leakage of charge to which capacitors are typically vulnerable. At $t_1$, the controller 142 has detected an arrhythmia and determines that therapy is needed. It immediately connects the output node 132 of the batteries to the converter 146, and cycles the FET 156 to initiate pulsed current flow to charge the capacitors.

The fast cell 126 immediately experiences a voltage drop to its loaded voltage of about 2.5V, and during the $t_1$–$t_2$ interval provides the bulk of the current to the load at about 2.0A for about 10 seconds. In response to the initial voltage drop across the fast cell 126, the dense cell 124 voltage begins to drop gradually, as current slowly flows from the dense cell 124 to the fast cell 126 and to the load, at a rate limited by the high internal resistance of the dense cell 124. During this charging interval, the capacitors are charged to a total voltage of 750–800V, and the voltages of both cells diminish slightly under the charging load.

At time $t_2$, the controller 142 has detected that the capacitors 150, 152 are fully charged, and disconnects the batteries 124, 126 from the converter 146. The high voltage capacitors 150, 152 are then caused to deliver their charge to the patient's heart via the leads. In practice, the discharge of the high voltage capacitors 150, 152 is a truncated exponential biphasic waveform that is delivered leaving about 100 to 200V on the capacitors 150, 152. This voltage then bleeds off over time or is the starting point for the next charge if another shock is needed to terminate the arrhythmia. However, for illustrative purposes the voltage is shown in the figure as dropping to zero. The controller 142 thus ceases the charging operations at $t_2$, and the cells 124, 126 are returned to a open circuit voltage. During the ensuing $t_2$–$t_3$ period, the primary activity is the flow of current from the dense cell 124 to the fast cell 126, initially at a rate of about 2 mA, and gradually diminishing. This recharges and readies the fast cell 126 for the next possible therapy delivery. During this period, the fast cell 126 voltage rises at a rate proportional its voltage difference from the dense cell 124, due largely to the recharging effect of the dense cell 124, but also because of voltage recovery as the load is eliminated. The dense cell 124 voltage also recovers slightly in spite of the load of charging the fast cell 126.

This recharging interval may vary widely in duration. In unusual circumstances, a patient may experience a ventricular tachycardia "storm" requiring about 10–15 therapy shocks in a short period. The fast cell 126 may provide this need without significant recharging, except that as its voltage drops, the time needed to recharge the capacitors increases. In normal circumstance in which there is a significant interval of hours or more between events, the dense cell 124 can fully recharge the fast cell 126. This permits a fast response to the next detected arrhythmia, reducing syncope concerns. With normally long recharging intervals, the fast cell 126 can remain ready at nearly its maximum voltage for the next event, so that therapy may be delivered promptly.

The dense cell 124 is selected to provide a typically flat voltage output over its life, so that as it is depleted, the fast cell 126 may be recharged to nearly the same voltage as when the cells were fresh. Further, even if the dense cell 124 were to diminish in voltage over time, this would not have a significant effect on the $t_1$–$t_2$ interval, but would only extend the $t_2$–$t_3$ interval, which is less medically critical in most instances. At time $t_3$, another arrhythmia is diagnosed, and the cycle is repeated.

In the preferred embodiment, the cells 124, 126 would be contained in a single metal housing 134 having two chambers, with the chambers sealed with respect to each other to isolate the different battery chemistries. This essentially provides a hybrid or composite battery with a compact package, and allows a short current path between the cells.

Figure 7:
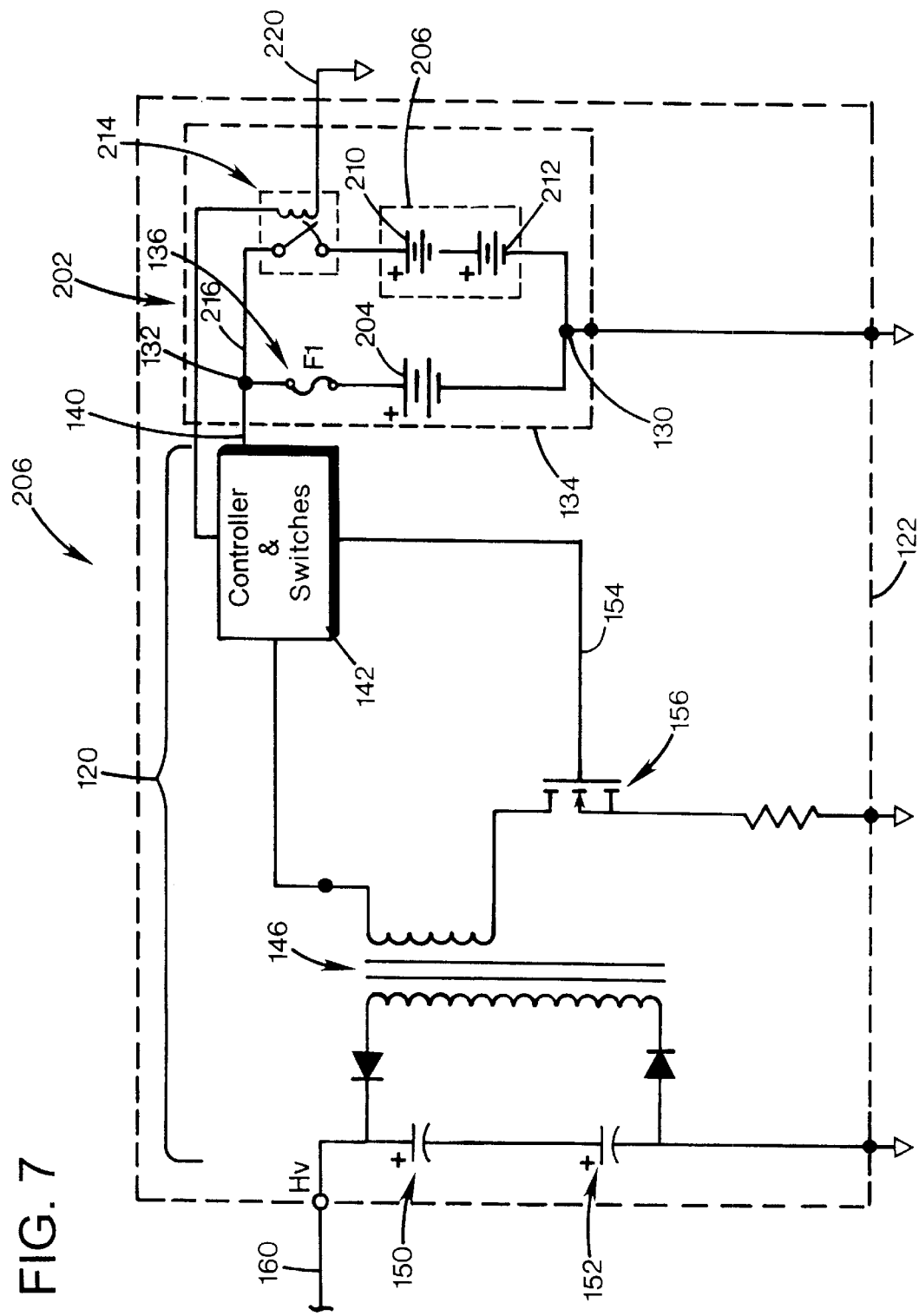
FIG. 7 is a schematic block diagram of an implantable defibrillator according to an alternative embodiment of the invention.

FIG. 7 illustrates an alternative implantable cardioverter/defibrillator (ICD) 200 containing a battery network 202 having a fast cell 204 connected in parallel with a dense cell set 206. The fast cell 204 is a Lithium Ion rechargeable cell with a carbon anode having a volume of 3 cc and an open circuit voltage of 4.1 volts when fully charged, and with the same current rating and other characteristics as the SVO in the preferred embodiment discussed above. The dense cell set 206 includes two Lithium Carbon Monofluoride (LiCF$_x$) cells 210, 212 (dense cells) connected directly in series to each other, the cathode of one connected directly to the anode of the other. Each of the dense cells 210, 212 is about half the volume of the dense cell 124 discussed above with respect to FIG. 1, and the set has a total open circuit voltage of 6.8V, significantly higher than that of the fast cell 204.

A normally closed relay 214 is serially connected between the dense cell set 206 and the output node 132, with a control line 216 operably connected to the controller, and a ground line 220. The relay 214 is operated selectively by the controller 142 to be open when the output node 132 is at a voltage above a threshold of 4.1V, and to close when the output node voltage 132 is below the threshold. The relay 214 opens and removes the dense cell set 206 from the circuit at 4.1V, and closes to include the dense cell set 206 in the circuit when the voltage drops below 3.8V. This permits charging of the fast cell 204 by the dense cell set 206 immediately when a capacitor-charging load is placed on the fast cell 204. By opening the relay 214 after the fast cell 204 is adequately charged and ready for the next event, leakage from the dense cell set 206 is prevented, and its energy is conserved. In addition, the significant voltage differential of 1.0V may allow fast recharging of the fast cell 204, while the ability to disconnect the dense cell set 206 prevents overcharging and the attendant energy loss.

An added benefit of the alternative embodiment of FIG. 7 is that any unavoidable leakage current from the always-connected fast cell 204 is not wasted, but is used by the system to operate the ongoing background functions of the controller and other device circuitry.

Protection Against Dendrite Formation During Charging

Figure 8:
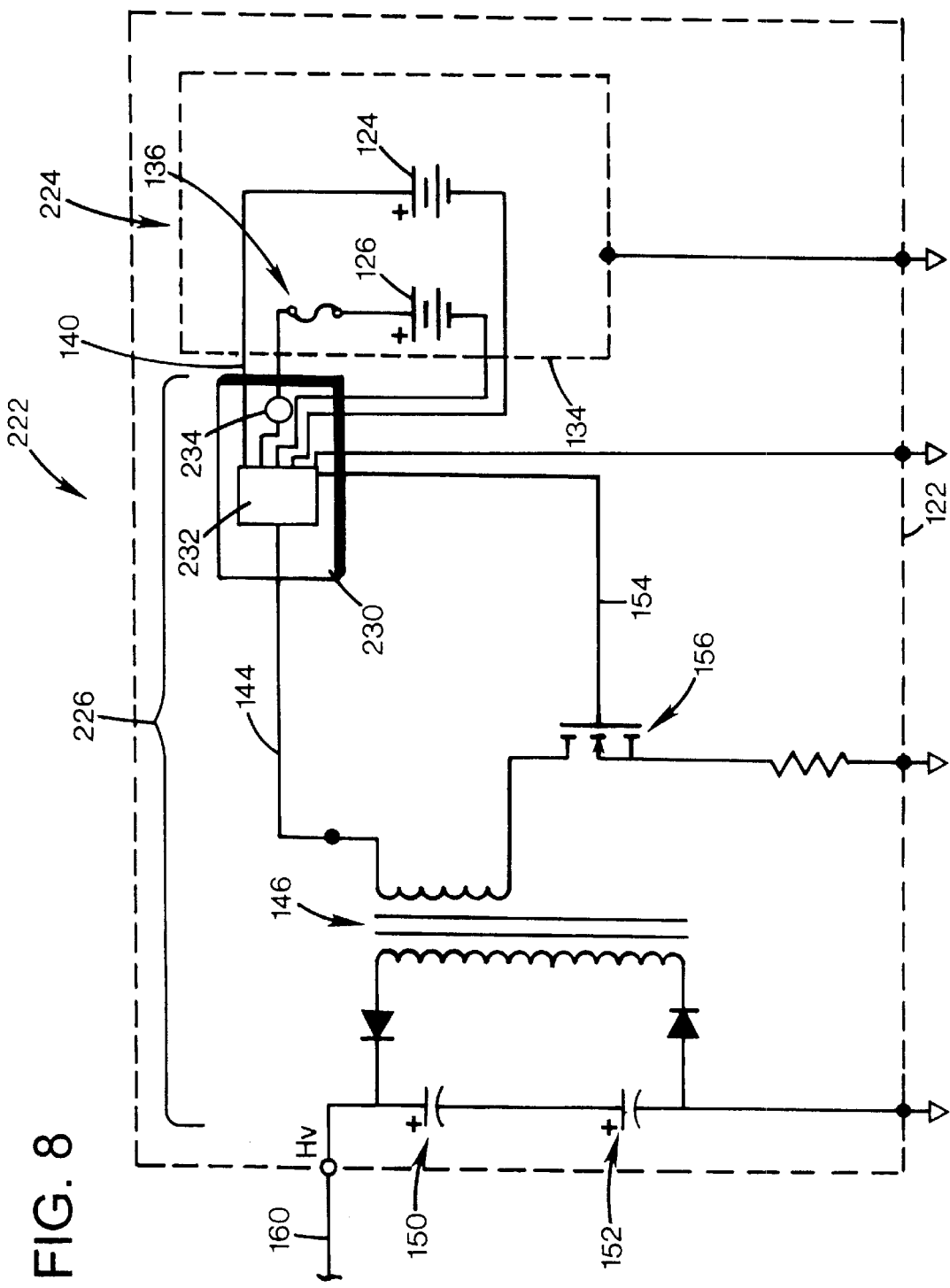
FIG. 8 is a schematic block diagram of an implantable defibrillator according to another alternative embodiment of the invention.

FIG. 8 shows an implantable cardioverter/defibrillator (ICD) 222 with additional circuitry for detection and correction of dendrite formation (i.e., which goes beyond the functions of monitoring and of blowing the fuse). The ICD contains a battery network 224 connected to defibrillator circuitry 226. As in the embodiment of FIG. 3, the battery network 224 includes a dense cell 124 and a fast cell 126. However, in this case, the batteries are not hard wired together in parallel. The anodes and cathodes of each battery are each connected independently to a controller and switch block 230, providing the ability to connect either battery selectively to other circuitry via the controller 230.

The controller 230 has switching circuitry 232 with a line leading to each electrode of each cell, and lines leading to ground and to the remainder of the defibrillator circuitry 226. The switching circuitry 232 has the capability to connect the cells 124, 126 together in parallel (cathode-to-cathode, anode-to-anode) for normal charging, to disconnect the batteries from each other, and to connect the batteries together in anti-parallel (cathode-to-anode, anode-to-cathode) for forced discharging. The connection to the remainder of the defibrillator circuitry 226 provides for capacitor charging in the manner discussed above with respect to the embodiment of FIG. 3.

The controller 230 also contains a current meter 234 capable of measuring the current flow on one of the lines connecting to the fast cell 126, so that current drawn by the fast cell 126 during charging may be monitored in real time.

During the normal operation in which the fast cell 126 is charged by the dense cell 124 following a delivery of therapy, the current meter 234 monitors the rate of current flow. While the internal impedance of the dense cell 124 (e.g. slow CFx) limits the current rate, the current meter serves to detect abnormalities in the current, so that connected monitoring circuitry (not shown) in the controller 230 may detect a fault and take action accordingly. Criteria for current abnormalities potentially indicating a short or dendrite formation in the fast cell 126 may include one or more of the following examples, alone or in combination:

1) an increase in the current above a preselected fixed value (e.g. current >75 mA),
2) an increase in the current above a stored nominal current curve, as a function of voltage, charge time, battery age/life or other factors (e.g. current >75 mA—67 x percent of battery life elapsed),
3) an increase in the current in excess of a preselected amount (in mA) within a limited preselected time interval (e.g. 10 mA in <1.0 seconds),
4) a percentage increase in the current in excess of a preselected amount within a limited preselected time interval (e.g. 10% increase in <1.0 seconds), or
5) a detected rate of change of the current value in excess of a preselected rate of change (e.g. >10 mA/sec).

In the preferred embodiment, a CFx battery for the dense cell 124 which has been used to maximum capacity and has an unloaded voltage of 3V, may have an initial internal impedance of 20 Ω, an end of life impedance of 200 Ω, with a current capacity of 150 mA at beginning of life, 15 mA at end of life, with about half those current values when drawn down at the end of a capacitor charging cycle. In such circumstances, a dead short arising in the SVO fast cell 126 due to a dendrite formation would cause current to flow at a maximum rate well above normal charging current levels.

A current spike of 5–20% should be detected within 0.1–10 seconds to trigger a response to possible dendrite formation. Preferably, the interval should be as short as possible to prevent a dendrite from growing to a robust size so that it can not be corrected. In the preferred embodiment, the circuitry is designed to respond within 0.1 seconds to detected current spikes. It is desirable to minimize this interval, but not to such a short interval that normal noise and variations are mistaken for faults. Because the current level during battery charging generally follows a gradually downward trending function, any increase in current may be indicative of a dendrite. However, limiting action only to those current increases in excess of a selected magnitude, and/or in a certain time interval serves to avoid false detection.

The circuitry responds to a selected current anomaly first by ceasing battery charging, typically by disconnecting the electrical connection made by the switching circuitry between the dense cell 124 and the fast cell 126. This prevents the further growth of a small dendrite. Then, in a simple system, an alarm may be activated to indicate to the patient that a fault has occurred, and that the device requires servicing. Such an alarm may be provided with vibration, or a slight low voltage shock to generate a tingling sensation or muscle twitching in the patient. During this time, either cell may be used to power detection circuitry, with any remaining charge stored in the fast cell 126 available for treatment required prior to device servicing.

Preferably, the device circuitry includes circuitry to automatically correct the dendrite formation without intervention or servicing. This is provided, in the illustrated embodiment, by connecting the cells 124, 126 in anti-parallel automatically. This generates a much higher current than would a simple shorting of the terminals, causing the dendrite to deplate. It is also possible that some dendrites may be thin enough to generate a high enough current density actually to fuse in the manner of a fusible link. In some embodiments, a simple brief shorting of the SVO terminals may be effective to deplate off most dendrites. In either case, the current flow through the dendrite is reversed relative to the charging process, so the effect of deplating on discharge works in concert to reduce the dendrite size (increasing its resistance), making burnout occur more readily, and conserving energy used. During this anti-parallel connection period, the device circuitry remains powered by the fast cell 126, which while depressed in voltage by the effect of the dense cell 124 (e.g. from 3.2V to 2.0V), has adequate capacity to power the circuitry. The fast cell 126 voltage will be depressed less than that of the dense cell 124 since the fast cell 126 cell has a much lower internal resistance. Some current limiting is necessary to prevent the dense cell 124 from being reverse biased, which could cause permanent damage to it.

Figure 9:
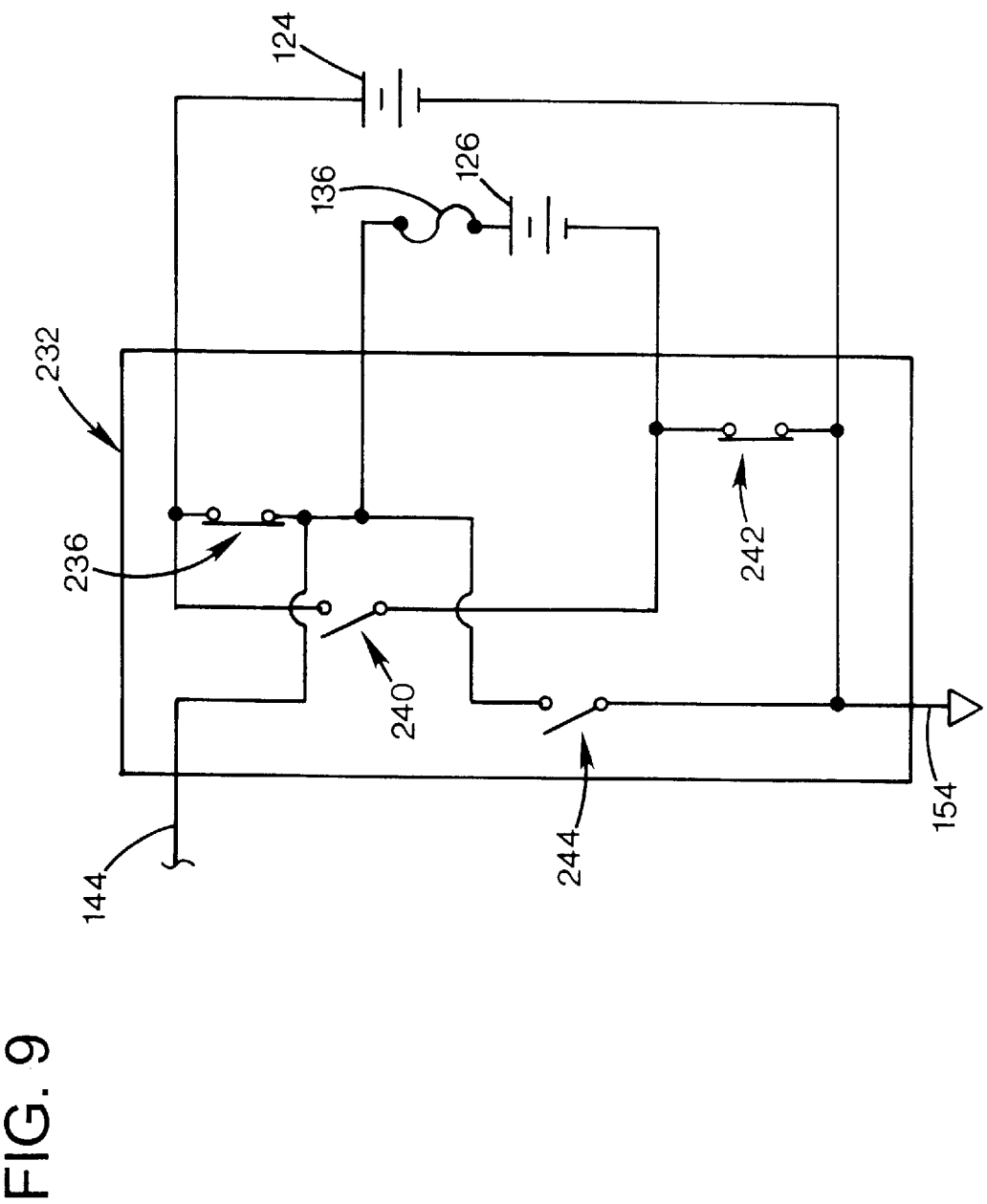
FIG. 9 is a schematic block diagram of switching circuitry according to the embodiment of FIG. 8.

FIG. 9 shows the switching circuitry 232 in greater detail, illustrating how the cells can be connected to each other in parallel and anti parallel, for the functions discussed above. The cathode of the fast cell 126 is connected to the power output line 144 without any intervening switch. The cathode of the dense cell 124 is connected to the power output line 144 via a switch 236, and to the anode of the fast cell 126 via a switch 240. The cathode of the dense cell is connected directly to control signal line 154, and to the cathode of the fast cell 126 via a switch 242. The anode of the fast cell is connected to the control signal line 154 via a switch 244. Switches 236 and 244 operate in concert as a linked pair, and are closed as shown to connect the batteries in parallel for charging, during which switches 240 and 244 remain open. Switches 240 and 244 are operated in concert and closed (while switches 236 and 244 are opened) to connect the cells in anti parallel for the purposes discussed above.

Figure 10:
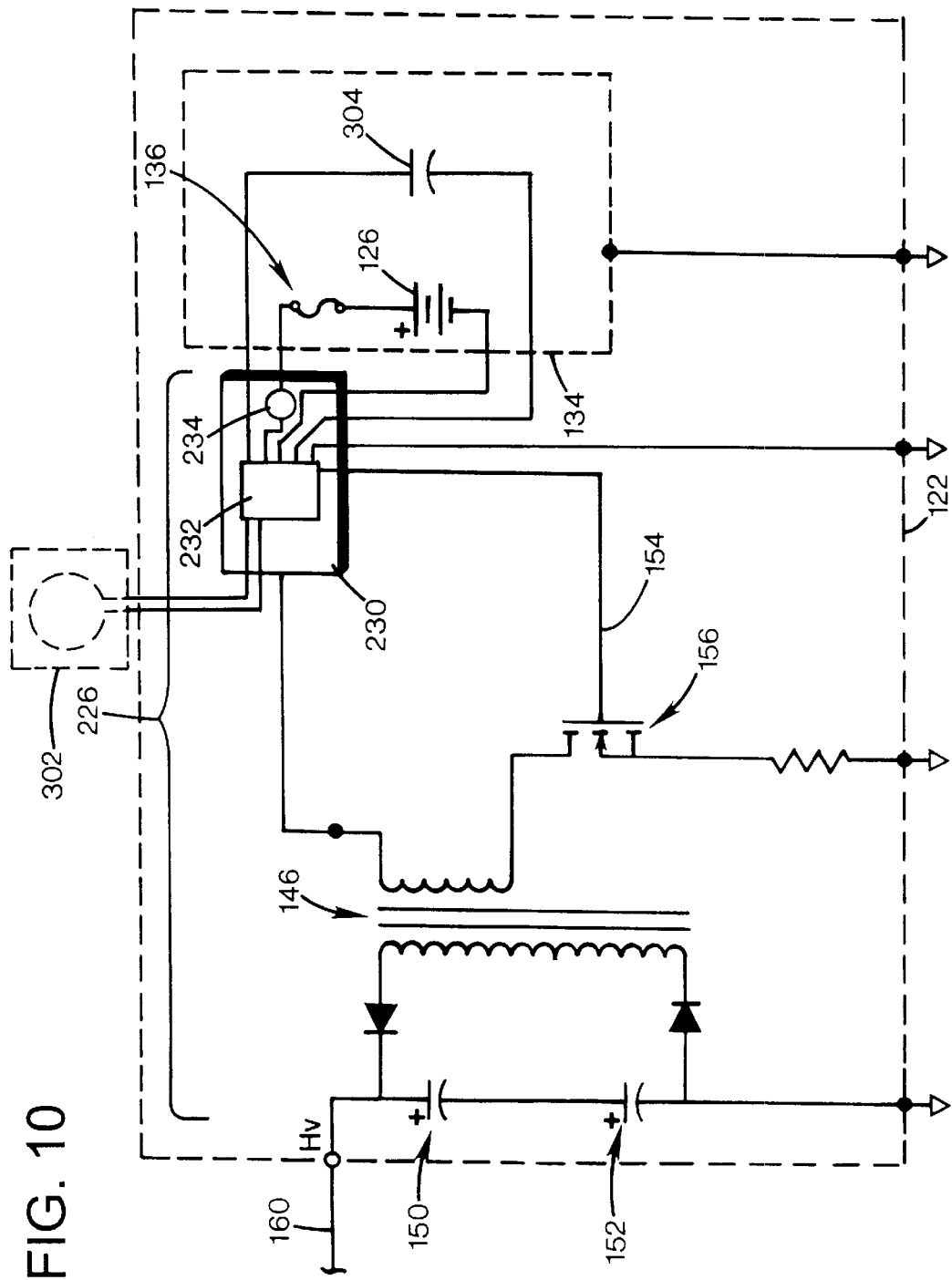
FIG. 10 is a schematic block diagram of an implantable defibrillator according to yet another alternative embodiment of the invention.

FIG. 10 shows an ICD device 300 having a single fast cell 126 that is periodically recharged from an external source via a transcutaneous inductive charger component 302 connected to the control circuitry 230 and switching circuitry 232. Should dendrite formation during charging be detected by the current meter 234, charging is stopped and a contrary current flow is generated. This may be generated by feedback to the external charger, which stops charging and reverses flow, or may be conducted by the control circuitry in the manner discussed above. This embodiment may also include a second cell, such as a dense cell to provide a greater energy storage capacity between external charges. A small capacitor 304 connected to the switching circuitry can be used to deliver the reverse current for dendrite removal. In this process, it is first rapidly charged by the fast cell 126 and then by capacitor 304, functioning in the manner of the dense cell 124 of FIG. 8.

While described in terms of a preferred embodiment, the invention need not be so limited. For instance, while discussed in terms of current monitoring for detection of dendrite formation, voltage monitoring may readily be employed. All references in the disclosure and the claims to current measurement are intended to intended to encompass voltage detection used to infer a current value.

What is claimed is:

1. An implantable cardiac rhythm management device, comprising:
   a pulse generator adaptively configured to generate electric shocks for delivery to a patient's heart comprising:
      at least one output capacitor;
      charging circuitry capable of charging the at least one capacitor to produce high voltage shocks for delivery to the patient's heart;
      a first battery, switchably coupled to the charging circuitry, having the characteristic of a high current flow rate to fast charge the at least one capacitor;
      a second battery, switchably connected in parallel to the first battery, having characteristics that enable the second battery to recharge the first battery;
      a detector, coupled to the charging circuitry that detects when the recharging current is above a predetermined threshold indicative of abnormal recharging within the first battery; and
      a controller programmed to switchably enable the charging circuitry to produce the high voltage shocks, and to disable the second battery whenever an abnormal recharging current is detected.

2. The device of claim 1 wherein the detector is operable to detect a percentage increase in the recharging current rate in excess of a preselected threshold.

3. The device of claim 1 wherein the detector is operable to detect an increase in the recharging current in excess of a preselected threshold, within a limited preselected time interval.

4. The device of claim 1 wherein the detector is operable a rate of change of the recharging current in excess of a preselected amount.

5. The device of claim 1 wherein the controller is operable, in response to detecting that the recharging current is above a predetermined threshold, to reverse the current flow to the first battery.

6. The device of claim 1 wherein the controller is operable to increase a plating thickness on an electrode of the first battery during charging, and operable, in response to detecting that the recharging current is above a predetermined threshold, decreasing the plating thickness on the electrode.

7. The device of claim 1 including switching circuitry operable to selectably connect the batteries together in anti parallel.

8. The device of claim 1 wherein the first battery is a Lithium Carbon Monofluoride cell.

9. The device of claim 1 wherein the second battery is a Lithium Silver Vanadium Oxide cell.

10. An implantable cardiac rhythm management device, comprising:
    capacitance means for providing a high voltage shock to a patient's heart;
    first power source means for fast charging the capacitance means using a high current flow rate;
    second power source means for providing a slow recharge current to the first battery
    detection means for detecting when the recharging current is above a predetermined threshold indicative of abnormal recharging within the first power source means; and
    control means for switchably coupling the capacitance means to the patient's heart when fully charged, and to disable the second power source means whenever an abnormal recharging current is detected.

11. The device of claim 10 wherein the first power source means is a first battery having the characteristic of a first current flow rate under a given load, and wherein the second power source means is a second battery having the characteristic of a second current flow rate less than the first current flow rate under the given load.

12. The device of claim 10 wherein the first power source means is a Lithium Silver Vanadium Oxide cell.

13. The device of claim 10 wherein the second power source means is a Lithium Carbon Monofluoride cell.

14. The device of claim 10 wherein the second power source means is a transcutaneous charging system.

15. The device of claim 10 wherein the detection means is operable to detect a percentage increase in the recharging current in excess of a preselected threshold.

16. The device of claim 10 wherein the detection means is operable to detect an increase in the recharging current in excess of a preselected threshold, within a limited preselected time interval.

17. The device of claim 10 wherein the detector is operable a rate of change of the recharging current in excess of a preselected amount.

18. The device of claim 10 wherein the control means is operable, in response to detecting that the recharging current is above a predetermined threshold, to reverse the current flow to the first power source means.

19. A method for recharging a high voltage shocking capacitor of an implantable cardiac rhythm management device, comprising the steps of:
    fast charging at least one high voltage shocking capacitor using a first battery having high current flow rate whenever a high voltage shock is needed;
    switchably coupling the at least one capacitor to the patient's heart when fully charged;
    recharging the first battery;
    detecting when the recharging current is above a predetermined threshold indicative of abnormal recharging within the first battery; and
    in response to detecting when the recharging current is above a predetermined threshold, disabling the step of recharging.

20. The method of claim 19 wherein recharging includes connecting a second battery to the first battery.

21. The method of claim 20 including connecting the batteries together in anti-parallel in response to detecting when the recharging current is above a predetermined threshold.

22. The method of claim 19 wherein detecting when the recharging current is above a predetermined threshold includes determining a rate of change of the recharging current.

* * * * *